US00PP33406P3

(12) United States Plant Patent
Kordes

(10) Patent No.: US PP33,406 P3
(45) Date of Patent: Aug. 31, 2021

(54) HYBRID TEA ROSE PLANT NAMED 'KORCARMSIS'

(50) Latin Name: *Rosa hybrida*
Varietal Denomination: KORcarmsis

(71) Applicant: W. KORDES' SÖHNE Rosenschulen GmbH & Co KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 16/941,861

(22) Filed: Jul. 29, 2020

(65) Prior Publication Data

US 2021/0092888 P1 Mar. 25, 2021

(30) Foreign Application Priority Data

Sep. 25, 2019 (QZ) ..... PBR 2019/2438

(51) Int. Cl.
*A01H 5/02* (2018.01)
*A01H 6/74* (2018.01)

(52) U.S. Cl.
USPC ..... Plt./138
CPC ..... *A01H 6/749* (2018.05)

(58) Field of Classification Search
USPC ..... Plt./130, 137, 138
CPC ..... A01H 5/0222
See application file for complete search history.

(56) References Cited

U.S. PATENT DOCUMENTS

PP8,279 P 6/1993 McGredy, IV
PP24,873 P3 9/2014 Meilland

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

A new and distinct variety of hybrid tea rose plant, referred to by its cultivar name, 'KORcarmsis', is described. The new variety forms in abundance on a substantially continuous basis attractive, cup like reddish-purple colored blossoms. The vegetation is vigorous, and the growth habit is very bushy and upright. Attractive semi-glossy, dark green foliage is formed. Additionally, the new variety is particularly well suited for growing as distinctive ornamentation in the landscape.

1 Drawing Sheet

Latin name of genus and species of plant claimed: *Rosa hybrida.*

Variety denomination: 'KORcarmsis'.

CROSS-REFERENCE TO RELATED APPLICATIONS

This application claims priority to Plant Breeders' Right Application Number 2019/2438, which was filed at Community Plant Variety Office in the European Union on Sep. 25, 2019, the contents of which are hereby incorporated by reference for all purposes.

BACKGROUND OF THE INVENTION

The new variety of hybrid tea rose plant of the present invention was created by controlled breeding in May 2008 in Sparrishoop, Germany by artificial pollination wherein two parents were crossed which previously had been studied in the hope that they would contribute the desired characteristics. The female parent (i.e., the seed parent) was an unnamed seedling (non-patented). The male parent (i.e., the pollen parent) of the new variety was a seedling from a cross of 'Macgenev' (U.S. Plant Pat. No. 8,279) x unnamed seedling' (non-patented in the United States).

The parentage of the new variety can be summarized as follows:

unnamed seedling x ('Macgenev' x unnamed seedling)

The seeds resulting from the above pollination were sown and small plants were obtained which were physically and biologically different from each other. Selective study resulted in the identification of a single plant of the new variety.

The new variety has been found to undergo asexual propagation at Wasco, Calif. and Cochranville, Pa. by a number of routes such as vegetative cuttings. Asexual propagation techniques in Wasco, Calif. and Cochranville, Pa., such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of hybrid tea rose plant of the present invention possesses the following combination of characteristics:

(a) abundantly and substantially continuously forms attractive, cup-like reddish-purple colored blossoms,
(b) exhibits a very bushy and upright growth habit,
(c) forms vigorous vegetation, and
(d) forms attractive ornamental semi-glossy, dark green foliage.

The new variety well meets the needs of the horticultural industry. It can be grown to advantage as attractive ornamentation in parks, gardens, public areas, and residential landscapes. Accordingly, it is particularly well suited for growing in the landscape.

The new variety can be readily distinguished from its ancestors. More specifically, the unnamed seeding seed parent displays a lower petal count and decreased disease resistance compared to the new variety. Additionally, the unnamed seedling pollen parent originating from the ('MACgenev' x unnamed seedling) cross displays a lighter flower color and a higher disease resistance compared to the new variety. Moreover, the new variety can be readily distinguished from non-parental related similar varieties. For example, 'Meitafnah' (U.S. Plant Pat. No. 24,873) displays less petals, a larger flower size, and a weaker purplish flower color compared to the new variety.

The new variety has been named the 'KORcarmsis' variety.

The first sale of the new variety was on Jul. 31, 2019 in Germany by the inventor or by another who obtained the new variety directly or indirectly from the inventor.

BRIEF DESCRIPTION OF THE PHOTOGRAPH

The accompanying photograph shows, as nearly true as it is reasonably possible to make the same in a color illustration of this character, a typical specimen of the new variety and blossoms of the new variety. The illustrated rose plant of the new variety was approximately two years of age and was grown outdoors in a three-gallon container on its own roots at Cochranville, Pa., U.S.A. in May 2020.

The drawing sheet illustrates a specimen of the plant displaying floral buds and flowers at varying points of opening.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on a two-year-old specimen of the new variety, observed during May, while growing on its own roots in a three-gallon container in Cochranville, Pa.

Botanical classification: *Rosa hybrida* cultivar KORcarmsis.

Plant:

*Height*.—Approximately up to 40.0 cm from the top of the soil plane.

*Width*.—Approximately up to 40.0 cm.

*Habit*.—Very bushy and upright.

Branches:

*Stem color*.—Old wood: commonly near Yellow-Green Group 146A — young stems: commonly near Yellow-Green Group 144A.

*Length*.—Main stems: approximately 40.0 cm on average. — secondary stems: approximately 16.0 cm on average.

*Diameter*.—Main stems: approximately 6.0 mm on average. — secondary stems: approximately 3.0 mm on average.

*Thorns*.—Young thorns: length is approximately 5.0 mm on average; width is approximately 3.0 mm at point of attachment; color is commonly near Red-Purple Group 60C; and amount is moderate, approximately 4 per internode. — old thorns: length is approximately 5.0 mm on average; width is approximately 3.0 mm at point of attachment; color is commonly near Greyed-Orange Group 177B; and amount is moderate.

Leaflets:

*Number*.—3, 5, and 7.

*Shape*.—Ovate; apex shape is acute to acuminate; and base shape is cuneate.

*Margin*.—Serrate.

*Undulation*.—Moderate.

*Texture*.—Upper surface: smooth. — under surface: smooth.

*Venation*.—Pattern: reticulate.

*Size*.—Terminal leaflet: length is approximately 5.5 cm on average; width is approximately 3.0 cm on average. — lower leaflets: length is approximately 3.5 cm on average; width is approximately 1.8 cm on average. — 5-Leaflet leaf: length is approximately 12.0 cm on average; width is approximately 9.5 cm on average.

Foliage:

*Young foliage*.—Upper surface color: commonly near Green Group NN137B blended with near Greyed-Red Group 178A towards the margins with venation of commonly near Greyed-Purple Group 183B. — under surface color: commonly near Greyed-Red Group 178A with venation of commonly near Greyed-Red Group 182B.

*Old foliage*.—Upper surface color: commonly near Yellow-Green Group 146A with venation of commonly near Yellow-Green Group 147B. — under surface color: commonly near Yellow-Green Group 147B with venation of commonly near Yellow-Green Group 147C.

*Petiole*.—Texture: upper surface is smooth; under surface glandular with some small prickles. — length: approximately 1.3 cm on average. — diameter: approximately 1.0 mm on average. — upper and under surfaces color: commonly near Green Group 138A.

*Rachis*.—Upper and under surfaces color: commonly near Green Group 138A. — length: approximately 6.5 cm on average. — diameter: approximately 1.0 mm on average.

*Stipules*.—Length: approximately 1.5 cm on average. — width: approximately 5.0 mm on average. — margin: Entire to erose. — upper and under surfaces color: commonly near Yellow-Green Group 144A.

Inflorescence:

*Number of flowers*.—About 6 blooms on average on a plant at once.

*Number of blossoms per stem or in a cluster*.—Typically, 1 bloom per stem on average.

*Blooming season*.—Typically, in bloom from May to November in Southeastern Pennsylvania.

*Peduncle*.—Color: commonly near Yellow-Green Group 144A. — diameter: approximately 4.0 mm on average. — length: approximately 4.0 cm on average. — surface texture: smooth.

*Sepals*.—Number: 7. — upper surface color and texture: commonly near Yellow-Green Group 144B, covered in short pubescence and some with a moderate amount of near Greyed-Red Group182B towards the central portion of the surface. — under surface color and texture: commonly near Yellow-Green Group 144B; puberulent. — size: length is approximately 2.5 cm on average; width is approximately 1.0 cm on average. — margin: entire. — apex: acute to aristate. — base: truncate as it joins the receptacle.

*Buds*.—Shape: ovoid. — size: length is approximately 2.0 cm on average; width is approximately 1.5 cm on average. — color (when opening): commonly near Greyed-Purple Group 186C.

*Flower*.—Form: double, cuplike. — profile: convex. — diameter: approximately 9.5 cm on average. — height: approximately 4.0 cm on average. — duration: on the plant approximately 10 days. — petal color when first and fully opened: upper surface is commonly near Red-Purple Group N74B with a small basal blotch near White Group 155A; under surface commonly near Red-Purple Group N74C with a very small basal blotch near White Group 155A.

*Petaloids*.—Upper surface color: commonly near Red-Purple Group N74B with a small basal blotch near White Group 155A. — under surface color: commonly near Red-Purple Group N74C. — number: 25. — length: approximately 2.0 cm on average. — width: approximately 1.5 cm on average.

*Fragrance*.—Very strong perfume scent.

*Petal*.—Number 65 on average. — drop: average. — length: approximately 4.5 cm on average. — width: approximately 4.5 cm on average. — overall shape: broadly obovate. — margin: entire with moderate undulation. — apex shape: rounded. — base shape: Cuneate. — texture: both surfaces are smooth.

*Stamen*.—Number: approximately 80. — anthers: number is approximately 80; color is commonly near Orange Group N25D; length is approximately 2.0 mm; shape is oval. — filaments: length is approximately 8.0 mm on average; color is commonly near Yellow Group 3B.

*Pistils*.—Arrangement: separate and free. — number: approximately 50. — style: length is approximately 5.0 mm; color of upper half is commonly near Red Group N45C; color of lower half is commonly near Greyed-Yellow Group 160D. — stigma: color is commonly near Greyed-Yellow Group 162B; diameter is less than 1.0 mm; shape is fan shaped.

*Receptacle*.—Size: 8.0 mm diameter. — depth: 1.0 cm. — shape: urn shaped. — color: commonly near Yellow-Green Group 144A. — surface texture: smooth.

*Pollen*.—None observed.

*Hips/seed*.—None observed.

Development:

*Vegetation*.—Semi-glossy, dark green, vigorous and strong.

*Blossoming*.—Abundant and substantially continuous from spring through frost.

*Resistance to diseases*.—Very good resistance for black spot (*Diplocarpon rosae*) and powdery mildew (*Sphaerotheca pannosa*).

*Pest resistance/susceptibility*.—Not observed to date.

*Hardiness*.—Hardy to USDA Zone 6b.

The new 'KORcarmsis' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of hybrid tea rose plant characterized by the following combination of characteristics:

(a) abundantly and substantially continuously forms attractive, cup-like reddish-purple colored blossoms, (b) exhibits a very bushy and upright growth habit, (c) forms vigorous vegetation, and (d) forms attractive ornamental semi-glossy, dark green foliage;

substantially as herein shown and described.

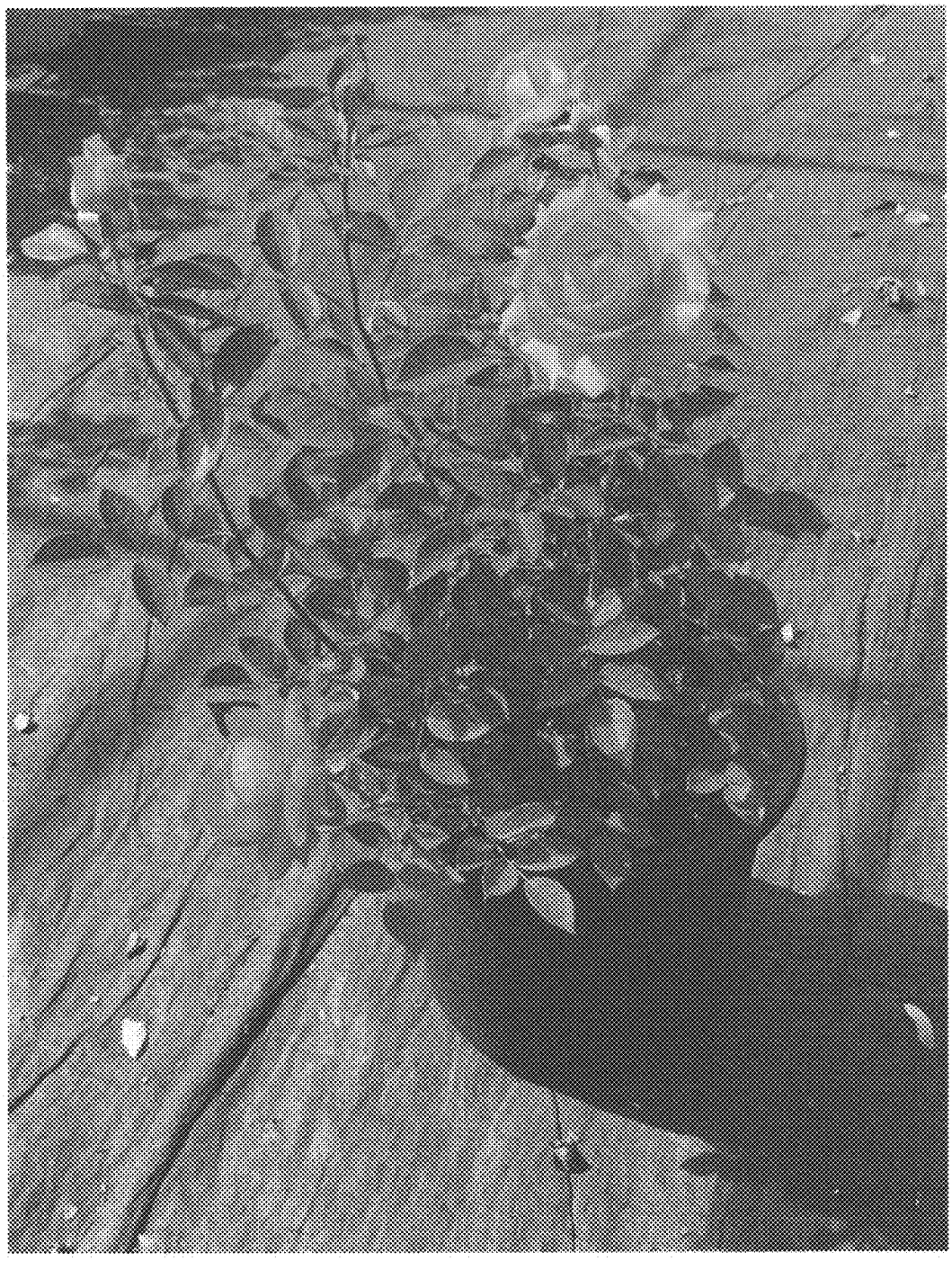

* * * * *